United States Patent [19]

Lawson

[11] Patent Number: 4,510,006

[45] Date of Patent: Apr. 9, 1985

[54] PERSONALIZED LAMINATED DISPLAY

[76] Inventor: A. David Lawson, 135 Suburban Rd., Knoxville, Tenn. 37923

[21] Appl. No.: 415,374

[22] Filed: Sep. 7, 1982

Related U.S. Application Data

[63] Continuation of Ser. No. 095,110, Nov. 16, 1979, abandoned.

[51] Int. Cl.[3] .......................... B44C 1/16; B32B 31/00; G09F 7/16; A61F 13/02

[52] U.S. Cl. .................................... 156/235; 156/240; 156/249; 156/254; 156/265; 40/595; 428/40; 428/914

[58] Field of Search ............... 156/235, 240, 239, 249, 156/234, 299, 277, 306.6, 264, 265, 344, 254, 267, 289, 300; 40/15, 2 R, 360, 594, 595, 596, 616, 615, 620, 593; 101/34; 428/914, 33, 40, 41, 42, 43, 456, 202; 427/147

[56] References Cited

U.S. PATENT DOCUMENTS

| | | | |
|---|---|---|---|
| 135,636 | 2/1873 | Dixon | 40/595 |
| 2,465,927 | 3/1949 | Rapp | 156/235 |
| 3,287,192 | 11/1966 | Pohlenz | 156/240 |
| 3,297,507 | 1/1967 | Twomey, Jr. | 156/240 |
| 3,640,009 | 2/1972 | Komiyama | 40/2.2 |
| 3,676,248 | 7/1972 | Swartz | 156/240 |
| 3,874,979 | 4/1975 | Hannon | 40/2.2 |
| 3,939,588 | 2/1976 | Hockaday | 40/2.2 |
| 4,153,496 | 5/1979 | Swift | 156/267 |

FOREIGN PATENT DOCUMENTS

| | | | |
|---|---|---|---|
| 2332581 | 11/1975 | France | 40/595 |

*Primary Examiner*—Edward Kimlin
*Assistant Examiner*—Louis Falasco
*Attorney, Agent, or Firm*—James C. Kesterson

[57] ABSTRACT

On-the-spot designed personalized laminated displays such as placemats, menus, posters and the like and the method of manufacturing same is disclosed. The laminated displays of this invention use inexpensive materials and are substantially unlimited in the final design, yet may be made or fabricated to order in a very short period of time while a customer waits. The method includes the selection of a backing sheet, the addition of selected decorative indicia, the addition of details and the like to the backing sheet, and adhesively securing personalizing alpha-numeric indicia, such as proper names and the like neatly, quickly, and effectively to the backing sheet to form the desired personalized display. The personalized display is then adhesively encased and sealed between two sheets of a transparent plastic film or the like for protection. Because of the new technique of adding decorative indicia and personalizing indicia to the backing sheet, the laminated display can be fabricated in a few minutes while a customer waits.

5 Claims, 17 Drawing Figures

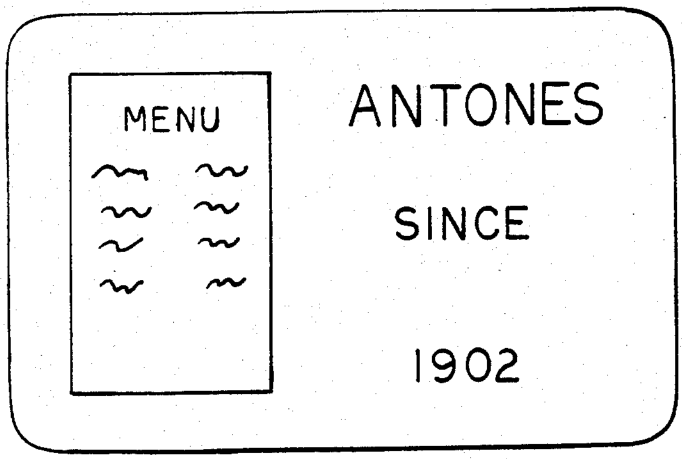
FIG. 5
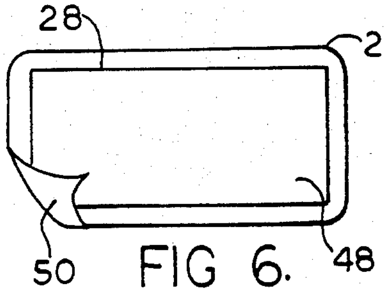
FIG 6.
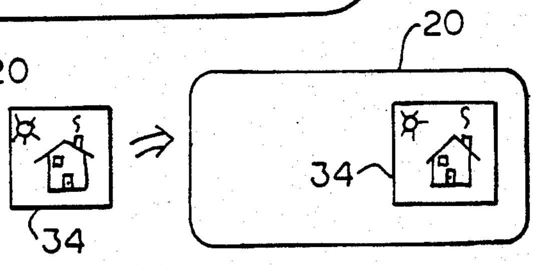
FIG. 7
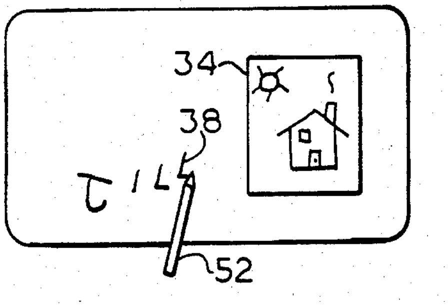
FIG. 8
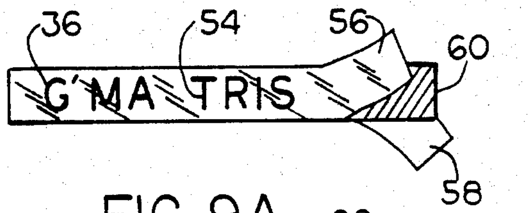
FIG. 9A
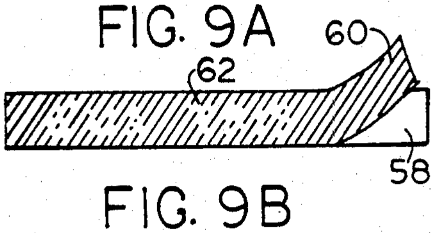
FIG. 9B
FIG. 9C
FIG. 10
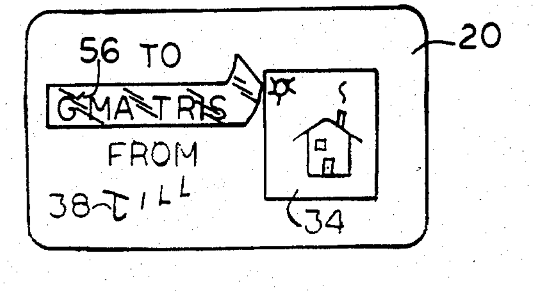
FIG. 11
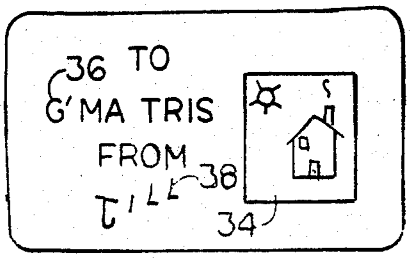

PERSONALIZED LAMINATED DISPLAY

BACKGROUND OF THE INVENTION

This application is a continuation of the U.S. application having Ser. No. 095,110 and filed Nov, 16, 1979, now abandoned.

This invention relates generally to the fabrication of laminated displays such as placemats, menus and posters, and more particularly to the on-the-spot production of personalized placemats and posters which may selectively use precisely shaped, precisely spaced and located alpha-numeric symbols of indicia for said personalization. The displays are produced by a fast and simple process which uses inexpensive materials.

Laminated displays such as placemats and posters are useful for many purposes including decorative, amusement and protective in both the home and business. For example, documents or pictures may be protected by lamination and then hung on a wall for display. It is also common knowledge that placemats are used to protect dining tables both in the home and commercial eating estabishments.

Heretofore, placemats or documents protected by lamination which were readily available from a department store or the like were always mass produced such that many hundreds or thousands, all identical, were produced and then sold to the retail outlet. By such methods, the cost is kept low, but the only way any personalization of the display by proper name or other techniques can be achieved is for the retail outlet to maintain a huge inventory of the display, which inventory includes substantially all of the possible proper names. It is apparent, of course, that it is virtually impossible to keep such an inventory and therefore most retail outlets maintain an inventor of personalized displays of only the most popular names. Thus, if an individual has an unusual name or an unusual spelling to his name, a personalized placemat or display typically just will not be available.

It is possible of course, to special order personalized laminated displays such as placemats, or menus etc., and in fact such personalized items are not uncommon with respect to commercial restaurants. In addition, it is also possible to have a particular, document, picture, poster, letter etc. protected by lamination such that the finished product is suitable for hanging on a wall for decoration. Unfortunately, such personalized displays are expensive and may require a substantial period of time such as weeks or months from the time the order is placed until delivery.

Therefore, it is an object of this invention to provide a method for quickly and inexpensively fabricating a personalized laminated display.

It is still another object of this invention to provide a method of producing a personalized display which uses precisely formed and precisely located alpha numeric symbols.

It is yet another object of this invention to provide a method of fabricating a laminated display which can be designed and fabricated on-the-spot.

Still another object of the invention is to provide a method of personalizing and protecting a selected display by lamination in a few minutes while a customer waits.

Other objects and advantages of this invention will become apparent upon reading the following detailed description together with the drawings.

SUMMARY OF THE INVENTION

To accomplish the above mentioned objects as well as other objects which will become evident from the following drawings and detailed description, the present invention dicloses a process for on-the-spot fabrication of a personalized laminated display such as a poster, placemat, menu and the like. The method comprises the steps of selecting an appropriate backing sheet having a first and a second side such as for example 80-pound bond paper. It will be appreciated that one or both of said first and second sides of the backing sheet may include a design. Any desired design or very thin decoration such as a decal, drawing on paper and the like is then adhesively applied to the backing sheet. Personalizing indicia such as precisely formed and precisely located alpha-numeric characters are then adhesively applied to the backing sheet to form the desired personalized display. The personalized display is then encased and sealed between two layers of transparent plastic film to produce said personalized laminated display. After laminating the personalized display, any excess plastic film may then be trimmed away.

Accordingly, the above mentioned objects and subsequent descriptions will be more readily understood by referenced to the following drawings wherein:

BRIEF DESCRIPTION OF THE DRAWINGS

FIG. 1 through FIG. 8 illustrates various examples of the finished personalized laminated displays.

FIG. 6 and FIG. 7 show the selection of a backing sheet and and the application of an example of decorative indicia.

FIG. 8 shows an example of still further personalization.

FIG. 9 shows an example of the preferred embodiment of providing precisely formed and precisely spaced alpha-numeric characters of an unusual proper name on an adhesive strip.

FIG. 10 and FIG. 11 show a proper name being applied in place to form the personalized display.

DESCRIPTION OF THE INVENTION

In this age of computers and numbers, it is always refreshing to receive a gift which is individualized or personalized. It is especially rewarding to get such a gift or an item with one's own name thereon. As was discussed heretofor, in the background of this application, personalized items having a name are typically limited to common names or are otherwise very expensive. For example, bicycle license plates with a child's name are readily available from a hardware store if the child's name is Jim, David, Mary, Betty or some other well known name. However, if the child's name is at all unusual or has a varied spelling, obtaining such a personalized bicycle license plates may well be impossible to find unless the plate is specially ordered. In a similar manner, name plates, placemats, posters, etc., etc., for unusual names just are not readily available. The present invention solves this problem for certain of these items such as posters and placemats in a manner which is not only completely universal with respect to a desired name, it can also help reduce the inventory of such items even less than that usually required if only well know names or personalized items are stocked.

Figure 1:
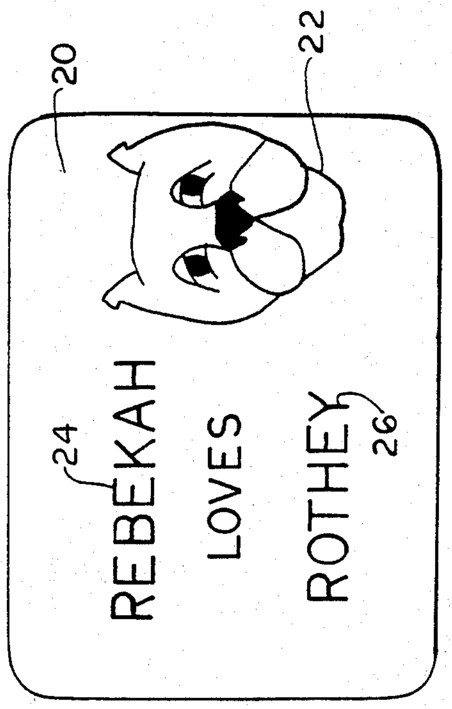

Referring now to FIG. 1 through FIG. 5, there is shown various samples of on-the-spot fabricated laminated displays which may be both very personal and suitable for use as a poster or a placemat. In particular, the laminated display of FIG. 1 illustrates how a backing sheet 20 may include a desired indicia already printed thereon. For example the drawing 22 could be a cat, dog, or other animal. However, of particular importance in this example is the unusually spelling of the name Rebekah 24 and the dog's name Rothey 26. It will be appreciated that although a shorten rendition of the name Rebekah such as "Becky" might be found on some standard personalized items, it is very unlikely that the full name Rebekah even with the common spelling Rebecca could be found, and it is almost certain that the old biblical spelling Rebekah could not be found. In addition, to also find a personalized item such as a poster or placemat which further includes the unusual name of a pet animal such as Rothey just simply is not going to happen.

Figure 2:
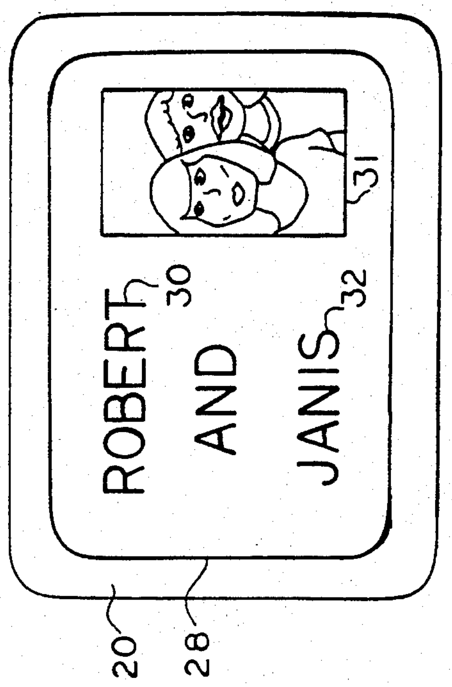

FIG. 2 illustrates still another example of a very personalized display. According to this example, the backing sheet 20 is preferrably plain, but could include a border such as shown at 28. Adhesively applied to backing sheet 20 is a selected photograph, painting, drawing or the like. The person in the photograph or other very personalized aspects can then be identified by the addition of proper names such as shown for Robert 30 and Janis 32. It will be appreciated, of course, that either of the two names could be very unusual or very common. However, in any event the possibility of the two names being included together is very remote if such personalized items were to be stocked. Also, of course, there is no way the item could contain the desired photographs or pictures. It will also be appreciated that according to this invention even three, four or more names could be included. However, the chances that all of the appropriate names would be included on a commonly stocked item are astronomically small.

Figure 3:
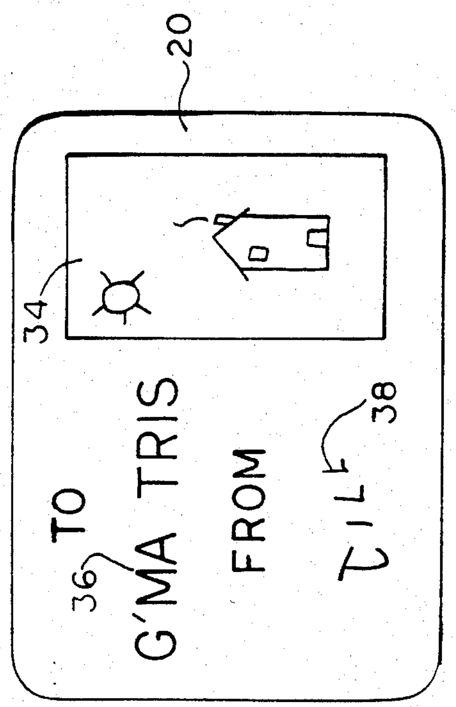

Parent and grandparents often wish to preserve a momento from their young children or grandchildren. For example, a child's drawing and signature is shown in FIG. 3. Details of how the design is fabricated on-the-spot will be discussed hereinafter. As seen in FIG. 3, the child's drawing 34 is applied with an adhesive to backing sheet 20. However, as can be seen, the drawing is dedicated to "G'Ma Tris" 36 which very personal name would not of course, ever be available as a stocked item. Finally, the child has by her own signature 38 signed the display.

Figure 4:
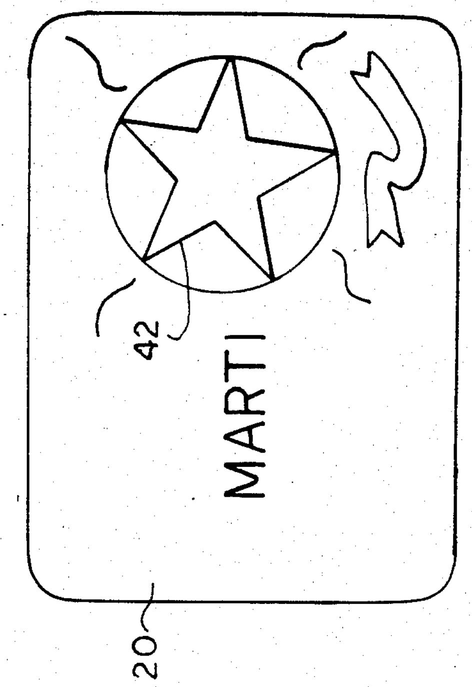

FIG. 4 illustrates how selective decal 40 can be transferred to the backing sheet 20. Also shown is another name having an unusual spelling.

FIG. 5 shows still another use for the method of this invention. It is well known that many restaurants, coffee shops and the like spend considerable amounts of money for their personalized menus. Other restaurants simply use plastic cases which protect the typed information on the menu. However, according to this invention there is an inexpensive and on-the-spot way of providing personalized laminated menus either in tablet or poster form or placemat form. According to FIG. 5, personalized indicia such as a name or logo 44 is applied to backing sheet 20. Also, shown at 46 is a listing of the offered food and its price.

Thus, it will be appreciated that the need and desire for very personalized displays is unlimited. Unfortunately, the time and expense of providng such personalized displays to date has been excessive. However, according to this invention there is now available a method of inexpensively fabricating such personal displays on-the-spot or in a matter of minutes. Referring now to FIG. 6 through FIG. 11, there is shown a step-by-step illustration of the various steps of the process of this invention for providing on-the-spot laminated displays. As shown in FIG. 6, a backing sheet 20 having a border 28 is selected. Backing sheet 20 may be selected from substantially any suitable sheet of material that will not be detrimentally affected by the heat and pressure experience during the encasing and sealing process to be described hereinafter. However, heavy bond paper selected from between 60-pound bond and 100-pound bond has been found to be suitable. According to a preferred embodiment, 80-pound bond paper has been found to be particularly suitable. Backing sheet 20 will of course, include a first or front side 48 and a back or second side 50. It will also of course, be appreciated that backing sheet 20 may be of any selective color, may be completely plain on both sides, or may include either elaborate or simple designs or indicia on one or both sides. For example, as was shown in FIG. 1, it might be desired to provide a stock of backing sheets which have an artists' rendition of a dog, a cat or another animal. Referring again to FIG. 6, there is shown a child's drawing 34 which is applied to backing sheet 20 by any suitable paper adhesive, that will not be detrimentally affected by the heat and pressure experienced during the laminating step. FIG. 7 shows how the drawing 34 is placed on sheet 20. As shown in FIG. 8, the child can "sign" backing sheet 20 which contains drawing 34 to provide a signature 38 by any suitable means such as a pen or a pencil 52.

Although a signature such as the child's signature 38 has in itself provided a very personal touch, it is often desirable to have a proper name (which may well be unusual in itself or have an unusual spelling) set out in precise and more formal style. Thus, FIG. 9 shows the unusual name "G'Ma Tris" 36 (for grandmother Trace) spelled out in a very precise form and having very precise spacing on a combination strip 54. It will be appreciated that it would seem that the name 36 could be applied by stencil, or could be made of peel-off letters. Unfortunately, the stenciling process is difficult and sometimes messy. Likewise, the peel-off letter approach although not too messy is very difficult to locate the letters and make sure they are properly spaced and aligned. Furthermore, both of these methods are very time consuming when properly accomplished. Thus the ability to fabricate the personalized display to the on-the-spot order is substantially lost if such methods are used. Therefore, of particular importance with respect to the fast process of this invention is the use of apparatus which can provide any desired name quickly, and precisely and in a form so that the name can be applied immediately to backing sheet 20, with correct spacing etc. To this end, a "Letter-On" machine available from Reynolds aluminum has been found to be particularly useful. Suitable apparatus such as the Letter-On machine includes a selection of letter dyes which can be used to cut a combination strip or "letter tape" discussed hereinafter. The letter dyes can be of a selected size and a selected font, including block, gothic, old english, modern, etc. However, the "letter tape" 54 used by such apparatus is the important aspect which makes it so particularly suitable for the process of this invention. Referring now to FIGS. 9A through 9C, there is shown how the letter tape is used. As shown in FIG. 9A, the letter tape 54 is comprised of three strips, a transparent slightly adhesive strip 56 and a slick or slightly waxed backing strip 58 such that backing strip 58 is not particularly receptive to an adhesive adhering thereto. The thin transparent strip 56 and backing strip 58 sandwich the colored letter strip 60. The colored letter strip 60, includes a strong adhesive on the side which is against backing strip 58, and is the source of the letters making up the name which will be placed on the backing sheet 20. Thus, because of the strong adhesive, letter strip 60 will adhere to backing strip 58, but not very well. To produce the letters making up the desired name, the letter dyes (not shown) are forced under pressure against the combination "letter tape". However, it is important to understand that transparent strip 56 is choosen to be thin and flexible enough so that when the letter dyes are used, transparent strip 56 is able to give or deform enough so that the dye does not cut through transparent strip 56. On the other hand, the inside colored letter tape 60 is thicker and is brittle enough such that the letter dye completely cuts through this tape even though it does not cut through the top transparent strip 56. Backing strip 58 is thick enough and separated far enough from the letter dye by strips 56 and 60 such that it is not cut by the dyes at all. Thus, it will be appreciated that when the "letter tape" is removed from the machine, only the letter strip 56 has the letters completely cut there through. Consequently, grasping letter strip 60 and backing strip 58 together while peeling off transparent strip 56, results in the desired letters adhering to the transparent strips 56 such as shown in FIG. 9C, while the waste material of letter strip 60 remains with backing strip 58. As shown in FIG. 9B, the waste material of letter strip 60, of course, leaves an outline 62 of the removed letters. The transparent strip 56, containing the desired letters or name 36 cut from letter strip 60 in a properly spaced manner is then carefully placed on backing sheet 20 at a desired location such as shown in FIG. 10. The letters are then held firmly in place on backing sheet 20 as the transparent tape 56 is peeled completely away thereby leaving the precisely formed letters (or name) 36 by themselves on the backing sheet in a precise alignment and precisely spaced manner. Thus, there is shown in FIG. 11 the desired personalized display which was also shown in FIG. 1. It will be apparent, of course, that none of the displays discussed to this point have been protected by lamination.

Figure 12:
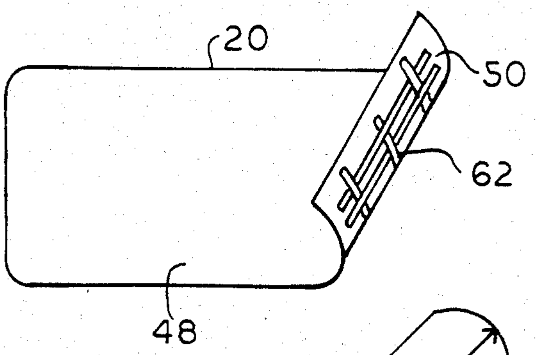
FIG. 12 shows an example of an alternate backing sheet having decorative indicia on its second or reverse side.

FIG. 12 shows how the second or backside 50 of backing sheet 20 may also include decorative indicia. For example, as shown in FIG. 12 backside 50 includes, printed thereon, a facsimile of woven grass cloth 62.

Figure 13:
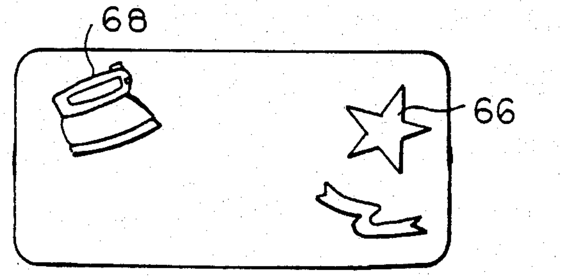
FIG. 13 shows an example of providing other decorative indicia such as iron-on decals to the front side of said backing sheet.

FIG. 13 illustrates how any selected decal can be transferred to front side 48 of backing sheet 20. As shown, iron-on decal 64 is transferred by an iron 68 to side 48 of backing sheet 20. The personalized name also can then be added in the same manner as heretofore discussed.

Figure 14:
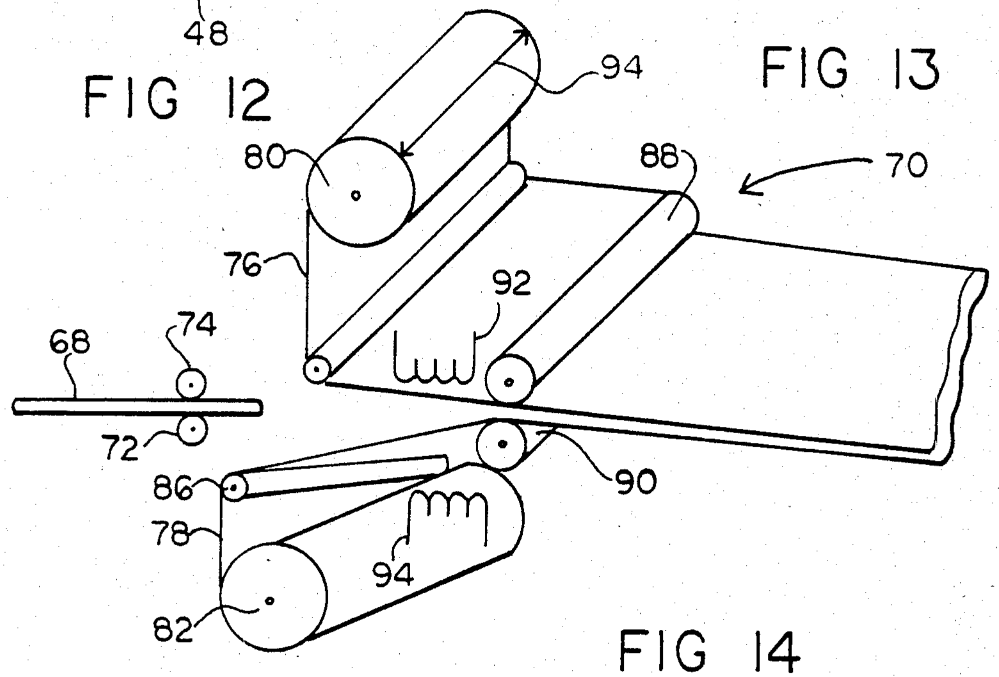
FIG. 14 illustrates the laminating process of protecting the personalized display.
Figure 15:
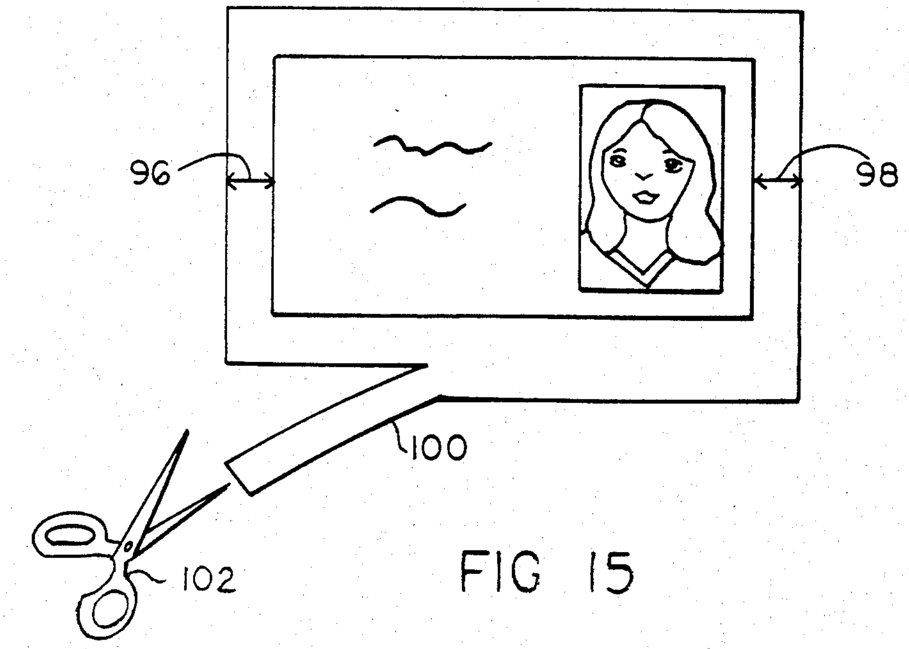
FIG. 15 illustrates the process of trimming the excess plastic film away from the personalized display.

Thus, it will be appreciated that there has been described various techniques of generating a seleted display which can be complete on-the-spot or in only a few minutes. However, it will be appreciated that regardless of whether the final personalized display is created by iron-on decals, drawings, letter tape etc. it is still very vulnerable to dammage, moisture, etc. Therefore, referring now to FIG. 14 there is illustrating the laminated process. As shown, the desired personalized display is passed through a laminating machine generally indicated at 70. The laminating machine 70, may be any suitable large laminating machine commercially available such as from Laminex Division, P. O. Box 577, Matthews, N.C. 28105 and General Binding Corporation, 1101 Skokie Blvd., North Brook, Ill. 60062. Although the machines obtained from different sources may vary somewhat, the basic process of lamination is similar. Thus, as is shown in FIG. 14, display 68 is passed between guide rollers 72 and 74 which gathers the display between two sheets of plastic film 76 and 78 which sheets are unrolled from roll 80 and 82. Film guide rollers 84 and 86 guide the film between press rollers 88 and 90. However, before sheets of flim 76 and 78 and arrived at press rollers 88 and 90, personalized display 68 is fed there between. Thus, personalized display 68 and the two sheets of plastic film 76 and 78 are all three passed between press rollers 88 and 90 which serve to encase and seal the display. It will be appreciated that most such lamination processes may also require the addition of heat to obtain a proper seal. Thus, electric heaters 92 and 94 are shown for purposes of providing heat to the plastic sheets 78 and 80 prior to the combination being passed between rollers 88 and 90. It will, of course, be appreciated by those skilled in the art that the width of plastic sheets 76 and 78 as indicated by arrow 94 is slightly greater than the width of the personalized display 68 being protected. Therefore, clear plastic film provides a more complete seal by extending beyond the edge of the display as is shown by arrows 96 and 98 in FIG. 15. It will also be appreciated that the roll of transparent plastic film includes an adhesive thereon that will "be set" by the heat and pressure from heaters 92 and 94 and press rollers 88 and 90. In addition, although the plastic film used in the invention step may be selected to have almost any thickness, it has been found that a plastic film between about 1.5 and 5 mils is suitable and that according to the preferred embodiment of this invention, a plastic film of about 3.5 mils is especially suitable. In addition, it has been found that at the time of passing the plastic film and the personalized display through the press rollers 88 and 90, the temperature may range between about 250° F. and about 350° F. but that a temperature of between about 275° F. to 300° F. provides superior results.

After the personalized display is sealed between the sheets of plastic film in a manner as discussed above, any excess film such as shown at 100 may be trimmed away by any suitable cutting means such as by scissors 102.

Therefore, although there have been described what are at present considered to be preferred embodiments of this invention, it will be obvious to those skilled in the art that various modifications may be made thereto without departing from the invention, and this invention is therefore intended of cover all such changes and modifications as fall within the true spirit and scope of this invention.

What is claimed is:

1. A method for fabricating on-the-spot personalized laminated displays comprising the steps of:

selecting a backing sheet having a first and second side, the first side being suitable for use as a background for a personalized display;

using a die to cut and form precisely shaped and precisely located lettes from a strip of letter material having a selected width, a top side and a bottom side, said bottom side having an adhesive applied thereto, said strip of letter material being sandwiched between a transparent strip and a backing strip, said transparent strip having an outside surface and an inside surface, said inside surface including an adhesive which forms a detachable bond with said top side of said strip of letter material, said backing strip including an adhesive resistant surface and a back surface, said adhesive resistant surface beng detachably bonded to said strip of letter material;

separating said transparent strip, and said formed letters from said letter material and said backing strip such that said precisely formed and spaced letters formed in said strip of letter material remain attached to said transparent strip, and all portions of said strip of letter material other than said precisely formed letters remain attached to said backing strip;

applying said precisely cut and formed letters attached to said transparent strip to said backing sheet to form said on-the-spot presonalized display;

peeling off said transparent strip such that said precisely formed letters are secured adhesively to said backing sheet and precisely located;

applying decorative indicia to said backing sheet, said decorative indicia including an adhesive on the side contacting said backing sheet;

encasing said personalized display between two sheets of transparent plastic film; and applying pressure and heat to said personalized display and said two sheets of plastic film to seal said personalized display therebetween to form said personalized laminated display.

2. The method of claim 1 and further including applying decorative indicia comprising the steps of providing a selected picture or figure with an adhesive on its reverse side and applying said selected picture or figure to said first to said backing sheet prior to said encasing step.

3. The method of claim 1 and further including applying decorative indicia comprising the step of transferring a decal to said first side of said backing sheet prior to said encasing step.

4. The method of claim 1 wherein said backing sheet is bond paper having a thickness between 60-pound bond and 100-pound bond, said plastic film has thickness between and 1.5 mils and about 5 mil, and said heat applied in said step of applying heat raises the temperature of said film to a temperature of between about 250° F. and about 350° F.

5. The method of claim 4 wherein said bond paper is 80-pound bond, said plastic film is 3.5 mil thick and said temperature is between about 275° F. and 300° F.

* * * * *